United States Patent [19]

Tomita

[11] Patent Number: 5,436,457
[45] Date of Patent: Jul. 25, 1995

[54] INFRARED GAS ANALYZER

[75] Inventor: Katsuhiko Tomita, Miyanohigashi, Japan

[73] Assignee: Horiba, Ltd., Japan

[21] Appl. No.: 252,574

[22] Filed: Jun. 1, 1994

[30] Foreign Application Priority Data

Jun. 10, 1993 [JP] Japan .................. 5-165218
Jun. 10, 1993 [JP] Japan .................. 5-165219
Jun. 12, 1993 [JP] Japan .................. 5-166224

[51] Int. Cl.⁶ .......................................... G01N 21/61
[52] U.S. Cl. .................. 250/343; 250/338.1
[58] Field of Search ............ 250/343, 345, 338.1

[56] References Cited

FOREIGN PATENT DOCUMENTS 0028622 2/1987 Japan ......................... 250/351
5-093650 4/1993 Japan ......................... 250/351

Primary Examiner—Paul M. Dzierzynski
Assistant Examiner—Richard Hanig
Attorney, Agent, or Firm—Poms, Smith, Lande & Rose

[57] ABSTRACT

A compact infrared gas analyzer capable of reducing the quantity of heat generated from a radiation source and the effects of temperature on samples is provided. A shutter is provided between the radiation source and the sample cell and/or between the sample cell and a detector with the shutter in a closed position. The shutter is opened and closed during measurement. A resistor comprising a resistance element made of one of $RuO_2$, W, $SnO_2$, FeCrAlY, Pt, Pt-Rh and Pt-Pd, formed on an AlN substrate, may be used as the radiation source, with the radiation source and the shutter being interrelatedly controlled.

30 Claims, 8 Drawing Sheets

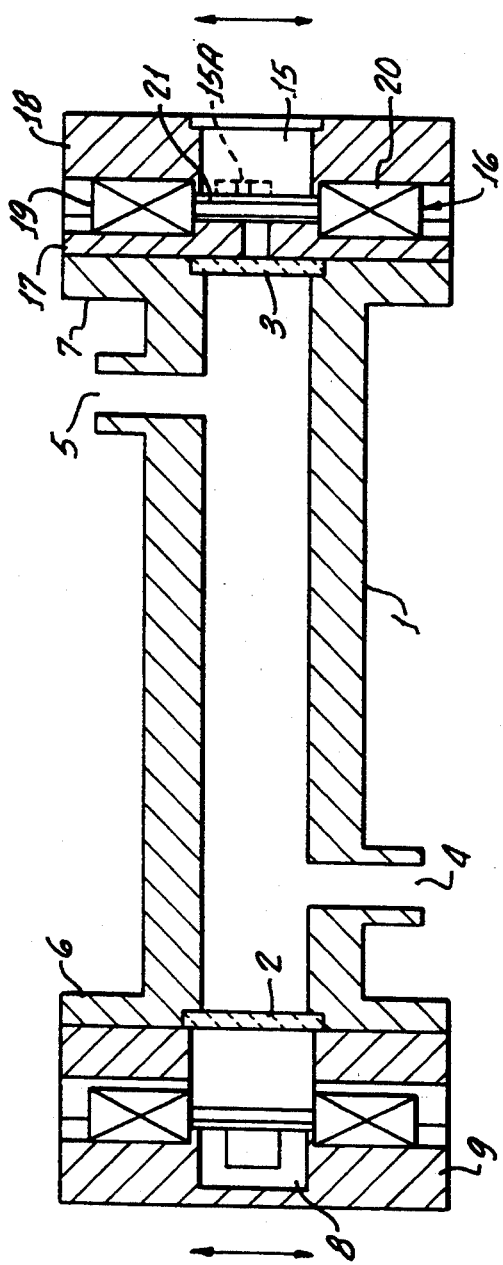
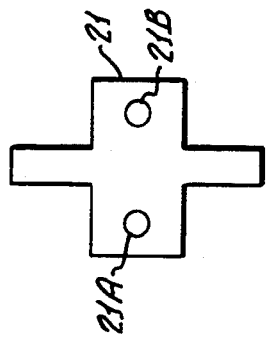
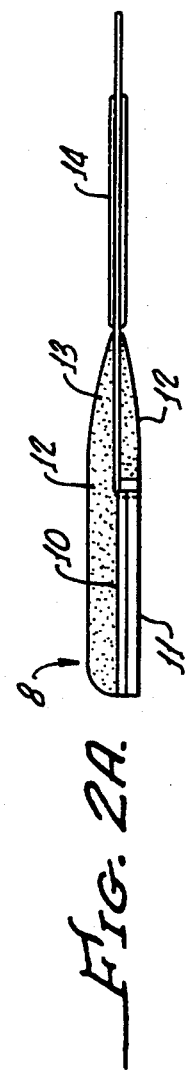
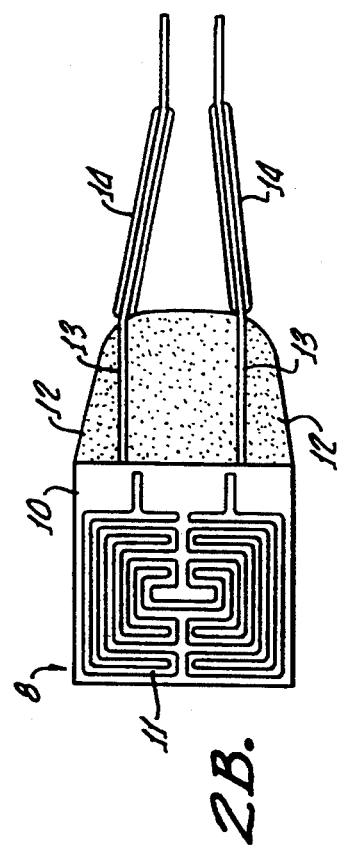

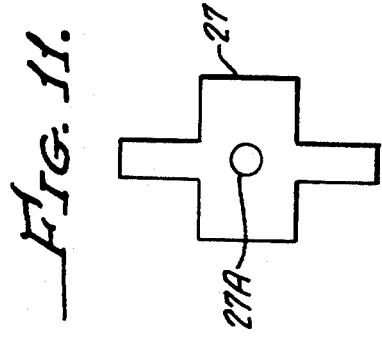
Fig. 11.
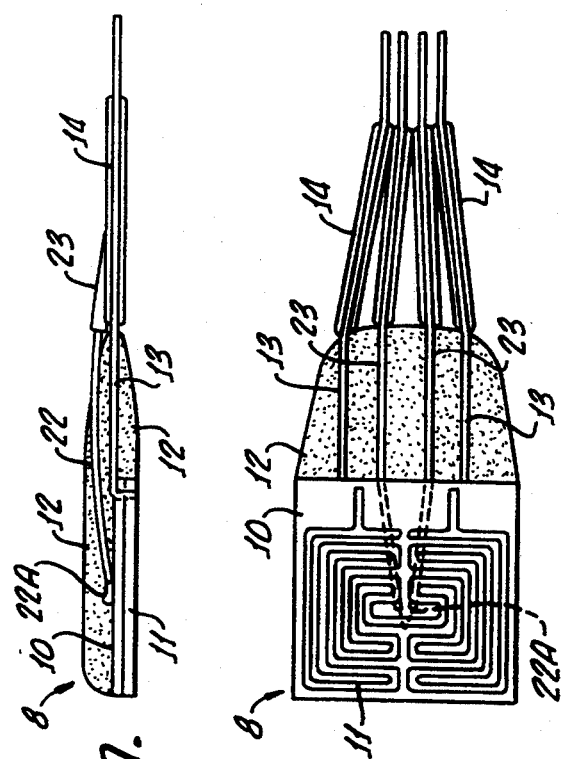
Fig. 9A.
Fig. 9B.
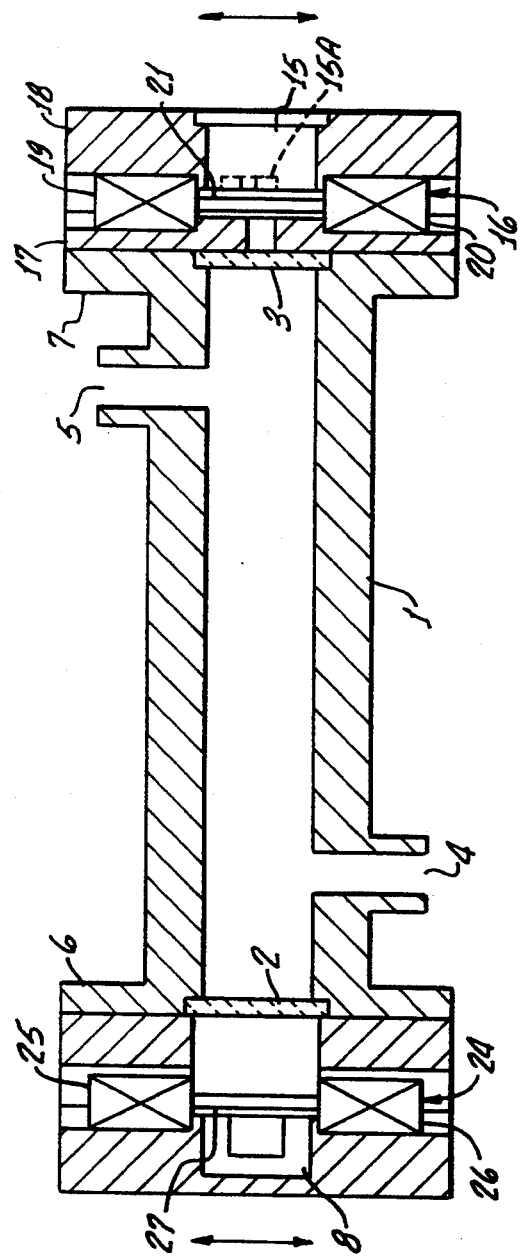
Fig. 10.

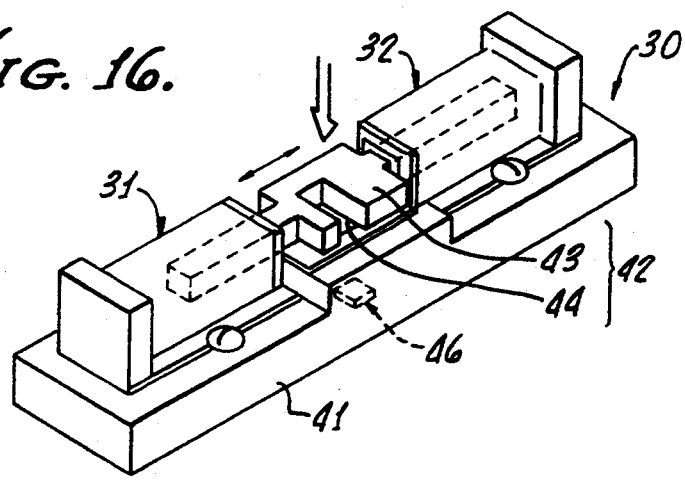
_FIG. 16._
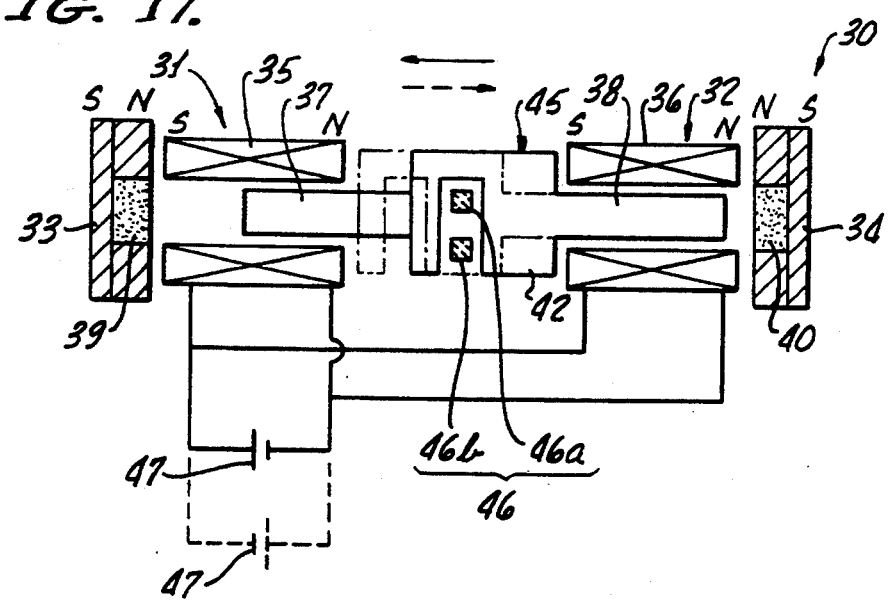
_FIG. 17._
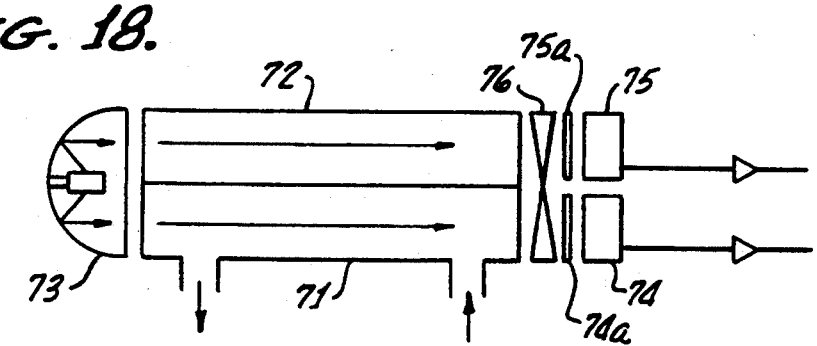
_FIG. 18._

INFRARED GAS ANALYZER

BACKGROUND OF THE INVENTION

1. Field of the Invention

The present invention generally relates to an infrared gas analyzer.

2. Description of the Prior Art

FIG. 18 shows a conventional infrared gas analyzer. Referring to FIG. 18, reference numerals 71, 72 designate a measuring cell and a reference cell arranged in parallel to each other. Although not shown in detail, both end portions of the respective cells 71, 72 are sealed with a cell window formed of infrared radiation transparent materials. Measuring cell 71 is supplied with a sample gas, as shown by the arrows, while the reference cell 72 is filled with a reference gas. Reference numeral 73 designates a radiation source at one end of cells 71, 72 used to transmit infrared radiation through cells 71, 72.

Reference numerals 74, 75 designate a detector comprising, for example, a pyrosensor placed at the end of cells 71, 72, respectively, for receiving infrared radiation passing through the cells 71, 72. Said detector 74 corresponding to measuring cell 71 is provided with a band pass filter 74a transmitting infrared radiation of a characteristic absorption band of a component gas to be measured (for example $CO_2$) therethrough while detector 75, corresponding to the reference cell 72, is provided with a band pass filter 75a transmitting infrared radiation having wavelengths out of said absorption band for said component gas to be measured. Reference numeral 76 designates a chopper arranged between cells 71, 72 and detectors 74, 75 and driven by a motor (not shown).

In the infrared gas analyzer described above, when measuring cell 71 is supplied with a sample gas and radiation source 73 is switched on to transmit infrared radiation through cells 71, 72 and chopper 76 is rotated, detecting signals are put out from detectors 74, 75 allowing a concentration of the component gas to be measured by analyzing the signals in an operating portion (not shown).

However, in the above-described conventional infrared gas analyzer, radiation source 73 is constantly on prior to measurement so that a temperature suitable for the measurement of the component gas may be arrived at while chopper 76 is continuously rotated. Thus, it takes considerable time and electric power for preparation prior to measurement and stabilization. In short, a conventional infrared gas analyzer can be said to be an energy consumption type. In addition, a disadvantage occurs in that heat generated when the radiation source 73 is active, and the motor is being rotated, as described above, is transmitted to detectors 74, 75, whereby said outputs of the detectors 74, 75 are influenced by a temperature-drift. Furthermore, chopper 76 is provided in addition to radiation source 73, cells 71, 72 and detectors 74, 75, so that a conventional infrared gas analyzer is undesirably large as a whole.

SUMMARY OF THE INVENTION

The present invention has been developed to overcome the problems of prior art infrared gas analyzers. It is an object of the present invention to provide a compact, easily handled infrared gas analyzer capable of reducing the quantity of heat generated from a radiation source.

In order to achieve the above-described objects, an infrared gas analyzer according to a first embodiment of the present invention is provided, in which a radiation source for emitting infrared radiation is provided on one end of a cell containing a sample gas, and a detector for receiving infrared radiation passing through the sample cell is provided at the opposite end of the cell to measure the concentration of a component gas in a sample gas. This analyzer is characterized in that a shutter, whose shutter body can be linearly opened and closed, is provided between the radiation source and the cell or between the cell and the detector with the shutter in a closed position when the radiation source is initially supplied with electric power. The shutter is opened by moving the shutter body when the temperature of the radiation source reaches a temperature high enough for the measurement of the component gas and remains open for a predetermined time. When the shutter is opened, optical communication is established between the radiation source and the detector through the sample cell. The power for the radiation source is switched off when the shutter is closed.

In a second embodiment of the present invention, an infrared gas analyzer is provided, in which a radiation source for emitting infrared radiation is provided on one end of cell containing a sample gas and a detector receiving infrared radiation passing through the sample cell is provided at the other end of the cell to measure the concentration of a component gas in the sample gas. This analyzer is characterized in that two shutters, having shutter bodies that are linearly opened and closed, are provided between said radiation source and the cell and between the cell and said detector respectively. The shutters are closed when the radiation source is initially supplied with electric power. The first shutter, on the side of the radiation source, is opened when the temperature of the radiation source reaches a temperature suitable for a measurement of the component gas establishing optical communication between the radiation source and the sample cell. The second shutter, on the side of the detector, is opened and closed at least one time during the time when the first shutter is open thereby establishing optical communication between the radiation source and detector. The first shutter is then closed, interrupting optical communication between the radiation source and the sample cell at approximately the same time the power to the radiation source is switched off.

In a third embodiment of the present invention, an infrared gas analyzer is provided, in which a radiation source for emitting infrared radiation is provided at one end of a cell containing a sample gas, and a detector for receiving infrared radiation passing through the cell is provided at the opposite end of the sample cell to measure the concentration of a component gas in the sample gas. This analyzer is characterized in that two shutters, having shutter bodies which are linearly opened and closed, are provided between the radiation source and the cell and between the cell and said detector respectively. The shutters are initially closed, with the first shutter, on the side of the radiation source, opening when the temperature of the radiation source reaches a temperature suitable for measuring the component gas and establishing optical communication between the radiation source and sample cell. The second shutter, on the side of the detector, is opened and closed at least once during the time when the first shutter is open thereby establishing optical communication between the radiation source and the detector. The first shutter on the side of the radiation source is then closed.

In a fourth embodiment of the present invention, an infrared gas analyzer is provided, in which a radiation source for emitting infrared radiation through a cell containing a sample gas is provided at one end of the sample cell, and a detector for receiving infrared radiation passing through the cell is provided at the opposite end of the cell to measure the concentration of a component gas in the sample gas. This analyzer is characterized in that a shutter is provided between said radiation source and the cell, or between the cell and said detector, in a closed position. The shutter is opened and closed during measurement to provide optical communication between the radiation source and the detector. A resistor comprising a resistance element made of one of $RuO_2$, W, $SnO_2$, FeCrAlY, Pt, Pt-Rh and Pt-Pd formed on an AlN substrate is used as the radiation source; the radiation source and the shutter being interrelatedly controlled. A resistance element made of positive temperature coefficient (PTC) materials containing $BaTiO_3$ may also be formed on said AlN substrate and used as a radiation source in this embodiment.

In addition, these radiation sources may be used in an infrared gas analyzer where a shutter is provided between the radiation source and the cell and between the cell and the detector respectively. The shutters remain closed until activated. A temperature sensor for detecting the temperature of the resistor used as the radiation source may be integrally incorporated in the resistor and used to activate the shutters.

In the infrared gas analyzer according to the first embodiment, when the temperature of the radiation source is kept at a temperature suitable for measurement of the component gas, the closed shutter is only opened for the time necessary for measurement and then closed. As soon as the shutter closes, power to the radiation source is terminated, and the emission of infrared radiation decreases shortly thereafter. During the time in which the shutter is opened (that is, the measuring time), the infrared radiation from the radiation source passes through the cell and is received by, for example, a dual-type pyrosensor provided with an element for use in a sample signal and an element for use in a reference signal to obtain the concentration of the component gas to be measured in the sample gas on the basis of a difference between outputs from both elements.

In addition, in the infrared gas analyzer according to the second embodiment, when the power source is switched on, the generation of infrared radiation increases the surface temperature of the radiation source. Initially, both the shutter on the side of the radiation source and the shutter on the side of the detector are closed. After switching on the power, the temperature of the radiation source is increased to a temperature suitable for measurement of the component gas. At this time, the first shutter, on the side of the radiation source, is opened, while the second shutter, on the side of the detector, remains closed. Consequently, the infrared radiation passing through the cell does not register upon the detector.

The second shutter is opened and closed, for example, twice, while the first shutter, on the side of the radiation source, is open. By opening and closing the second shutter, the infrared radiation emitted from the radiation source and passing through the cell intermittently registers upon a dual-type detector provided with an element for use in a sample signal and an element for use in a reference signal. The two signals put out from the dual-type detector are capable of measuring the concentration of the component gas in the sample gas from the average value of the two output signals.

It must be noted that, as used herein the term "optical communication" is not in any way limited to visible radiation but rather applies to radiation of all wavelengths including infrared radiation.

After completion of the measurement, the first shutter, on the side of the radiation source, is closed and the power to the radiation source is switched off. Simultaneously, the second shutter, on the side of the detector, is closed to prepare for the following measurement.

According to the first and second embodiments, the radiation source emits infrared radiation in a pulsewise manner. Conversely, according to the third embodiment, the radiation source continuously emits infrared radiation. After the completion of the measurement, both the shutter on the side of the radiation source and the shutter on the side of the detector are closed.

According to the fourth embodiment, the radiation source is provided with a resistance element made of $RuO_2$, W, $SnO_2$, FeCrAlY, Pt, Pt-Rh and Pt-Pd or PTC materials containing $BaTiO_3$ formed on the AlN substrate. AlN has superior characteristics in that thermal conductivity is increased; radiation emitted, heat uniformity and electric insulation are all improved; the coefficient of expansion is reduced; mechanical strength is increased; and thermal shock resistance is improved despite the ceramic make-up of the material.

Accordingly, the resistor comprising the resistance element formed on a substrate made of AlN has advantages in that electric characteristics and mechanical characteristics are remarkably superior, consumption of electric power is reduced, and useful lifetime is prolonged.

In addition, in the case where the resistance element is made of the PTC materials containing $BaTiO_3$, consumption of electric power can be reduced even more.

Moreover, in the case where the sensor detecting the temperature of the resistor is integrally incorporated in the resistor, the temperature of the radiation source can be more accurately detected, increasing the sensitivity of the analyzer.

Other objects, features and advantages of the present invention will be apparent to those skilled in the art from a consideration of the following detailed description of preferred exemplary embodiments thereof taken in conjunction with the Figures which will first be described briefly.

BRIEF DESCRIPTION OF THE DRAWINGS

FIG. 1 is a diagrammatic cross-section showing an infrared gas analyzer according to one preferred embodiment of the present invention;

FIG. 2A and FIG. 2B show one example of a radiation source used in the infrared gas analyzer of the present invention, FIG. 2A being a sectional view and FIG. 2B being a plan view;

FIG. 3 is a plan view of a shutter body on the side of a detector;

FIG. 9A and FIG. 9B show an exemplary radiation source of the present invention; FIG. 9A being a sectional view and FIG. 9B being a plan view;

FIG. 10 is a diagrammatic cross-section showing an exemplary infrared gas analyzer;

FIG. 11 is a plan view of a shutter body on the side of a radiation source in an infrared gas analyzer, according to the teachings of the present invention;

FIG. 16 is a perspective view showing an exemplary shutter according to the present invention;

FIG. 17 is a schematic diagram showing principal components of an exemplary shutter of the present invention; and FIG. 18 is a diagram showing construction of a prior art infrared gas analyzer.

DETAILED DESCRIPTION OF THE PREFERRED EMBODIMENT

Figure 4:
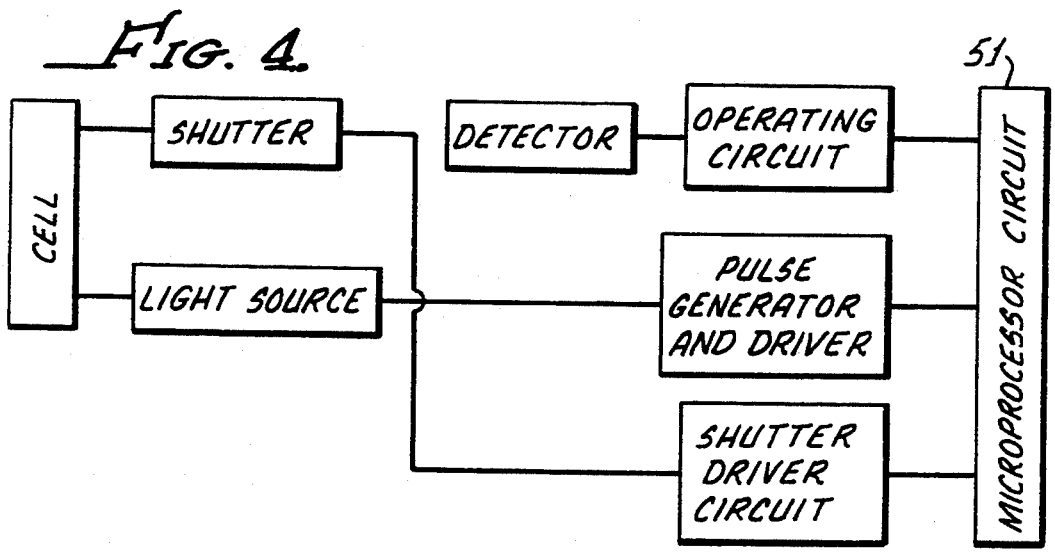
FIG. 4 is a block diagram showing one example of a control system in the infrared gas analyzer.

Embodiments of the present invention will be described below with reference to the drawings.

FIGS. 1 to 3 show one embodiment of the present invention. Referring to FIG. 1 first, reference numeral 1 designates a cylindrical sample cell made of corrosion resistant materials, for example, stainless steel, sealed with cell windows 2, 3 made of infrared radiation-transparent materials at both ends thereof and provided with an inlet port 4 of a sample gas and an outlet port 5 of said sample gas. The sample gas is introduced into said cell 1 through said inlet port 4 by means of a suitable suction pump (not shown) and then discharged from cell 1 through outlet port 5. In addition, reference numerals 6, 7 designate flange portions formed at both ends of the cell 1.

Reference numeral 8 designates a radiation source provided on one end of the cell 1 for emitting infrared radiation. Said radiation source 8 is comparatively small-sized and has radiating temperature-change characteristics as shown in, for example, FIG. 6. Reference numeral 9 designates a radiation source holder.

In addition, a radiation source shown in FIG. 2 may be used as one example of radiation source 8 emitting said infrared radiation. That is to say, referring to FIG. 2, reference numeral 10 designates an AlN substrate of several mm square, said AlN substrate 10 is provided with a resistance element 11 formed by printing a thick film made of one of $RuO_2$, W, $SnO_2$, FeCrAlY, Pt, Pt-Rh and Pt-Pd to form a fine resistance pattern, followed by baking on an upper surface thereof. A surface of an AlN substrate 10 is formed as a radiating portion. Reference numeral 12 designates an insulating overcoat layer, reference numeral 13 designating a lead-taking out Ag wire, and reference numeral 14 designating a polyimide-clad wire.

A suitable DC current can be applied to the radiation source 8 having the above described construction and its temperature can be increased after about 20 to 60 seconds from a start of application of the DC current. The maximum rated power of the radiation source 8 is 9 W (the power density is 100 $cm^2$).

According to a measurement of a temperature change by means of a radiant thermometer, the temperature increases to 450° C. after about 60 seconds from application of a DC current of 4.5 V when starting at room temperature under normal atmospheric conditions. This increase is shown by curve A in FIG. 7.

Reference numeral 15 designates a detector provided on the opposite end of the sample cell 1 and comprises, for example, a dual-type pyrosensor. A measuring interference filter 15A and a reference interference filter 15B (not shown) are arranged on radiation-receiving surfaces of said detector 15 so as to face said sample cell window 3 through a shutter 16, which will be described in detail below, said filters oriented perpendicular to the moving direction of said shutter 16 (the direction shown by a double arrow in FIG. 1). Reference numeral 17 designates a shutter holder and reference numeral 18 designates a detector holder.

A shutter which is biased in a closed position and whose movable portion is linearly moved when a signal is put therein is preferably used. Such a shutter is described in Japanese Patent Application No. 4-193127.

FIGS. 16, 17 show a shutter or electromagnetic wave-interrupting device 30 of double solenoid type which is described in the aforementioned patent application. Referring to FIGS. 16, 17, reference numerals 31 and 32 designate a self-holding solenoid comprising a fixed iron core 33, 34, a coil 35, 36 wound in the same direction, a movable iron core 37, 38 and a permanent magnet 39, 40, respectively. Said self-holding solenoids 31, 32 are arranged in a line.

In this embodiment, for example, an N-pole is arranged closer to said movable iron core 37 in the self-holding solenoid 31, while, in the self-holding solenoid 32, an S-pole is arranged closer to said movable iron core 38, so that polarities of said magnetic poles of said permanent magnets 39, 40 may be alternately reversed. Reference numeral 41 designates a base frame for placing the self-holding solenoids 31, 32 in a desired position.

Reference numeral 42 designates a shading portion provided between the self-holding solenoids 31, 32 and supported by connecting them with movable iron cores 37, 38. Said shading portion 42 is made of materials capable of blocking electromagnetic waves such as infrared radiation, including, for example, plastics, iron, aluminum, stainless steels and lead (effective for X-rays and the like), and provided with an opening 44 at a part of the shading portion 42. In short, one movable member 45 is formed by the movable iron cores 37, 38 and the shading portion 42. In addition, reference numeral 46 designates a dual type pyrosensor comprising, for example, two radiation-receiving elements 46a, 46b.

In said electromagnetic wave-interrupting device 30 having the above described construction, when said coils 35, 36 of the self-holding solenoids 31, 32 are connected with each other in parallel, as shown in FIG. 17, and a certain DC pulse signal (one-shot signal) is given to the coils 35, 36, magnetic fields are generated in the same direction in the respective self-holding solenoids 31, 32.

When a DC power source 47 is connected, as shown by a solid line, under the condition that the movable iron cores 37, 38 are positioned as shown by a solid line in FIG. 17, and radiation arrives at said detector 46, a force attracting the movable iron core 37 to the side of the permanent magnet 39 acts in the self-holding solenoids 31, while, a force repelling the movable iron core 38 from the side of the permanent magnet 40 acts in the self-holding solenoid 32, to bias said movable member 45 in the direction shown by a solid arrow, thereby moving the shading portion 42 in the same direction, so that the detector 46, which has been in a radiation-receiving configuration, is shaded from radiation. That is, optical communication between the radiation source and detector 46 has been interrupted. Movable iron core 37 is held by the permanent magnet 39 to keep the self-holding solenoid 31 in that condition.

On the other hand, in the case where the DC power source 47 is connected in such a manner as shown by a broken line when the movable iron cores 37, 38 are positioned as shown by broken lines and the detector 46 is shaded, forces opposite to the above-described forces act in the self-holding solenoids 31, 32, so that the movable member 45 is moved in the direction shown by the broken arrow thereby moving the shading portion 42 in the same direction, so that the detector 46, which has been shaded from radiation, assumes a radiation-receiving configuration. That is, optical communication between the radiation source and detector 46 is established. The movable iron core 38 is held by the permanent magnet 40 to keep the self-holding solenoid 32 in that condition.

As described above, the movable member 45 comprising the movable iron cores 37, 38 and the shading portion 42 can be biased by putting control signals having the same polarities in the coils 35, 36, so that the detector 46 can be switched from the radiation-receiving configuration to the shaded configuration, and vice versa. If pulsewise control signals, different in polarity, are alternatively given to the coils 35, 36, they can be used as the shutter, the chopper or the like.

Thus, in the infrared gas analyzer according to the above-described embodiment of the present invention, the electromagnetic wave-interrupting device 30 operated on the basis of the above-described operating principle is applied to provide the shutter 16 comprising the self-holding solenoids 17, 18 and the shutter body 19 between the cell 1 and the detector 15, as shown in FIG. 1. The shutter body 19 corresponds to the movable member 45 in FIGS. 16, 17. In addition, the shutter body 19 is provided with two openings 19A, 19B formed at near center thereof, as shown in FIG. 3. Sizes of and the distance between openings 19A, 19B are adjusted to those of the filters 15A, 15B of the detector 15.

FIG. 4 is a block diagram showing one example of a construction of a circuit in the infrared gas analyzer.

Figure 5:
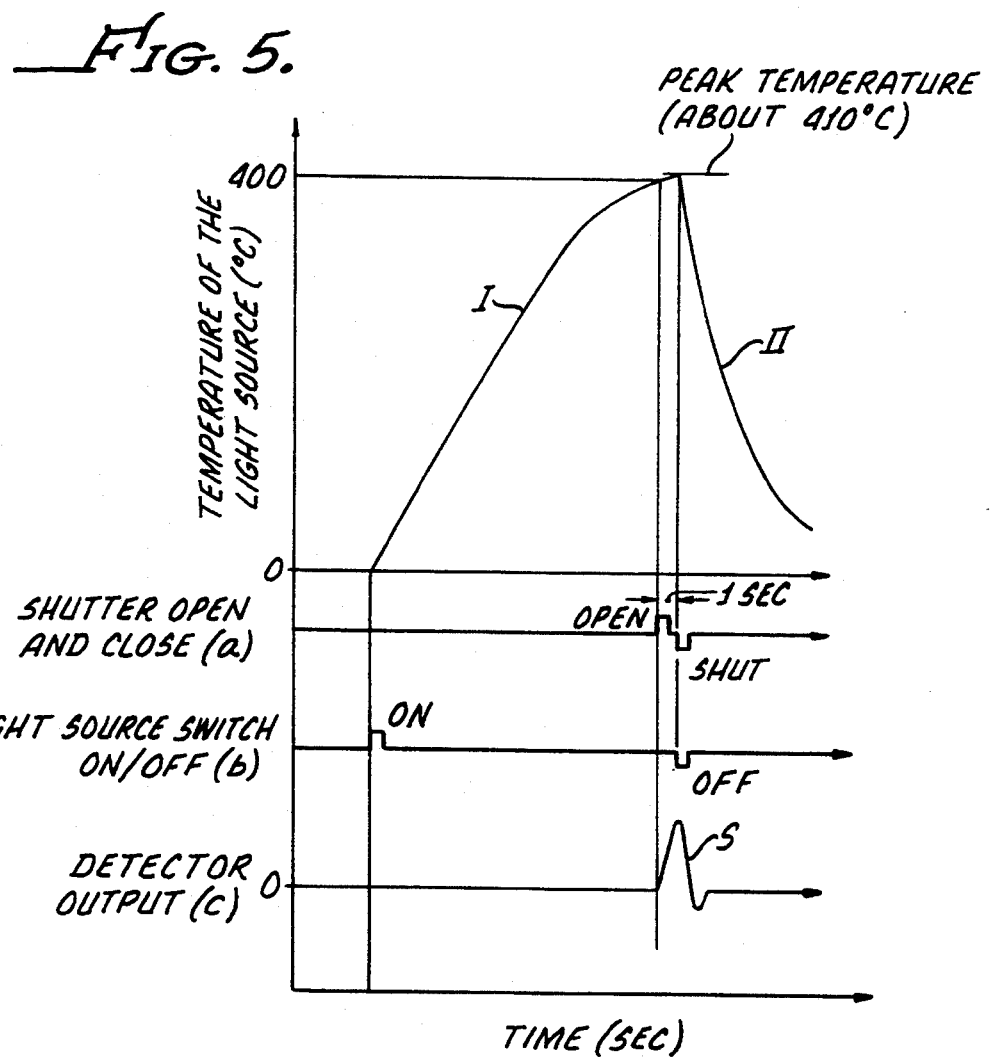
FIG. 5 is a graphical representation of the operation of an infrared gas analyzer, in accordance with the teachings of the present invention.

Next, operation of the infrared gas analyzer having the above-described construction will be described with reference to graphical representation in FIG. 5.

Initially, before the start of measurement, the shutter 16 is closed. That is to say, openings 21A, 21B of a shutter body 21 exist at positions different from the filters 15A, 15B of the detector 15 to shade detector 15 from radiation.

1. When a button is operated to switch on the power source [refer to (b) in FIG. 5] under the above-described condition, the radiation source 8 emits electromagnetic radiation. At this time, a pump is driven to supply the inside of cell 1 with sample gas. Although the surface temperature of the radiation source 8 is nearly 0° C. before the power source is switched on, the radiation source 8 is heated by switching on the power source to increase the temperature as shown by curve 1 in FIG. 5. At this time, although the infrared radiation from the radiation source 8 is transmitted through the cell 1 toward the detector 15, the shutter 16 is closed so that the infrared radiation does not reach the detector 15.

2. When the surface temperature of the radiation source 8 reaches a temperature suitable for measurement of the component gas, for example, about 400° C., the shutter 16 is operated to move the shutter body 21 and thus move the openings 21A, 21B of the shutter body 21 to the positions of the filters 15A, 15B of the detector 15, whereby the shutter 16 is opened [refer to (a) in FIG. 5] establishing optical communication between radiation source 8 and detector 15.

3. The shutter 16 is opened for the time necessary for the measurement of the component gas, for example, about 1 second, and then closed [refer to (a) in FIG. 5]. The supply of electric power to the radiation source 8 is stopped at the same time as the closing operation of the shutter 16 [refer to (b) in FIG. 5].

4. The surface temperature of the radiation source 8 further increases slightly after shutter 16 is opened, even though the electric power is not supplied, and gradually decreases as shown by a curve 11 in FIG. 5 after a peak (for example about 410° C.). Although it is desirable for the surface temperature of the radiation source 8 to be lowered to nearly room temperature following the measurement, about 50° C. is sufficient.

Figure 6:
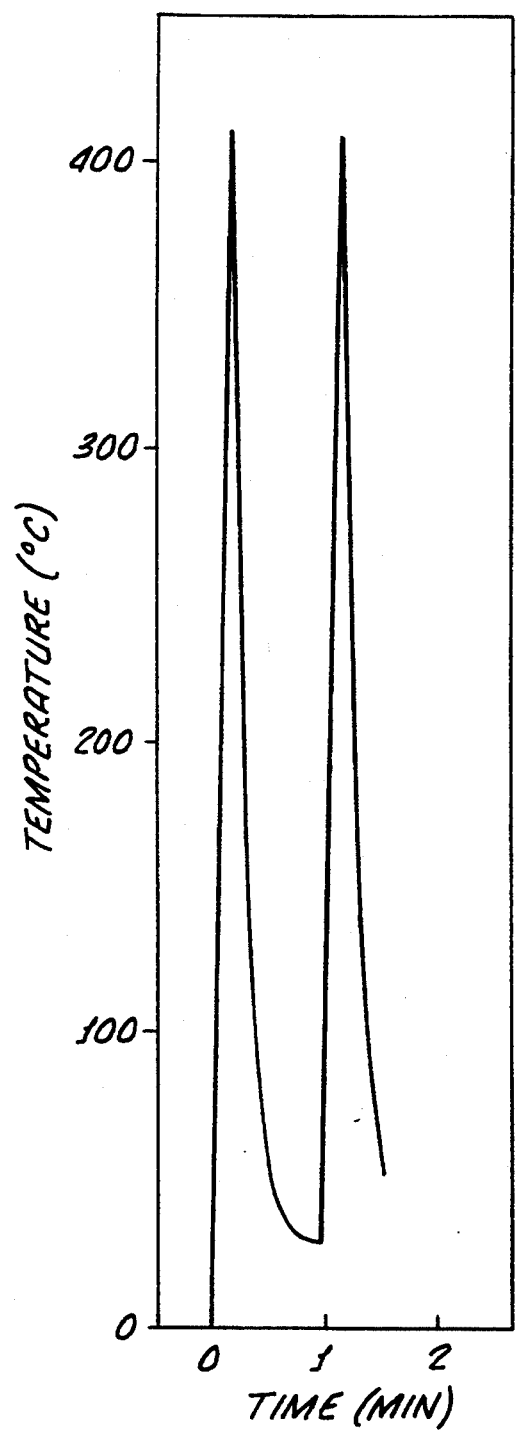
FIG. 6 is a graph showing radiating temperature-change characteristics of the radiation source in the infrared gas analyzer.
Figure 7:
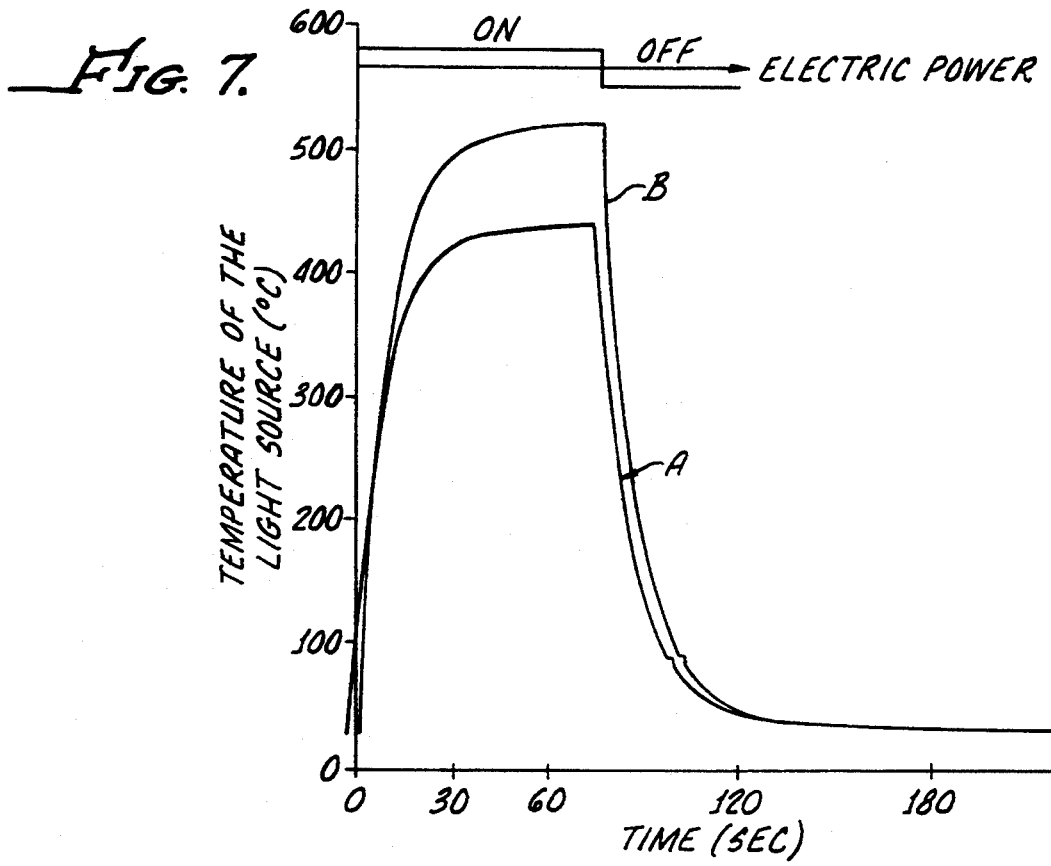
FIG. 7 is a graph showing radiating temperature-change characteristics of a radiation source used in the present invention.

The above-described steps 1 to 4 give one measuring cycle. Such a measuring cycle is controlled by the microprocessor circuit 51 shown in FIG. 3. In short, the time until the surface temperature of the radiation source 8 arrives at the temperature suitable for the measurement after the radiation source 8 was switched on can be previously set by the use of the radiating temperature-change characteristic graph as shown in FIGS. 6, 7. Accordingly, the desired operation can be conducted by programming the above-described steps 1 to 4 in said microprocessor circuit 51.

The present invention is not limited by the above-described embodiment but can be modified. For example, although the measurement is intermittently conducted in the above described preferred embodiment, a circuit capable of freely setting the time of the above described one measuring cycle to, for example, 1 to 60 minutes may be provided so that intermittent measurement and continuous measurement of the sample may be selected.

Figure 8:
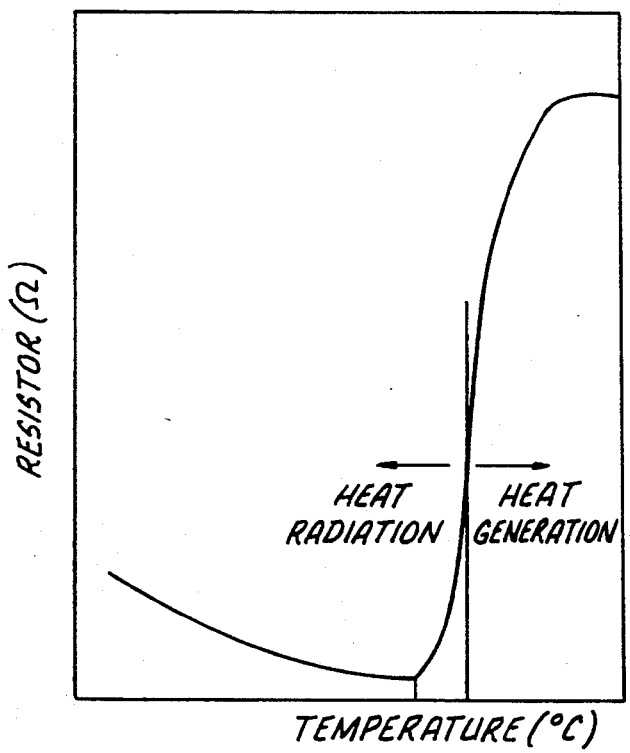
FIG. 8 is a graph showing temperature-characteristics of PTC materials.

The resistance element 11 of the resistor as the radiation source 8 may be made of PTC (Positive Temperature Coefficient) materials containing $BaTiO_3$. That is to say, a PTC thermoresistor having a positive temperature coefficient is obtained by adding a very small quantity of compounds of rare earth elements (for example $Y_2O_3$, $La_2O_3$ and the like) to sintered bodies of $BaTiO_3$ family as bases control valence orbitals and thus act as semiconductors. They are heated to markedly (about 3 orders of magnitude) change the resistance thereof as shown in FIG. 8. Consequently, the consumption of electric power can be significantly reduced by using such radiation source.

Referring to FIGS. 9A & 9B, a hot point of contact 22A of a thermocouple 22, such as alumel-chromel, used as a temperature sensor may be spliced to a back side of the resistor, of which resistance element 11 is made of one of $RuO_2$, W, $SnO_2$, FeCrAlY, Pt, Pt-Rh and Pt-Pd, or the resistance element 11 made of the PTC materials containing $BaTiO_3$ to draw out through a lead wire 23. In the radiation source 8 having the above-described construction, the surface temperature of the radiation source 8 arrives at 520° C. 60 seconds from the time when the electric power was switched on. That is to say, the temperature characteristics of the radiation source are much improved.

Although the shutter 16 is arranged between the cell 1 and the detector 15 in the above described preferred embodiment the shutter 16 may be arranged between the radiation source 8 and the cell 1.

Furthermore, individual shutters may be arranged between the radiation source 8 and the cell 1 and between the cell 1 and the detector 15, respectively. The construction in these embodiments will be described below.

FIG. 10 shows the infrared gas analyzer not only provided with the second shutter 16 between the sample cell 1 and the detector 15, but also provided with an equivalent first shutter 24 between the radiation source 8 and the sample cell 1. That is to say, first shutter 24 comprises self-holding solenoids 25, 26 arranged at a suitable interval therebetween and a first shutter body 27. First shutter body 27 is provided with one opening 27A formed at near center thereof, as shown in FIG. 11. Said opening 27A is adjusted to the radiation source 8 in size and position.

Other components are the same as those in the infrared gas analyzer shown in FIG. 1, so that the corresponding parts are designated by the same reference numerals and their descriptions have been omitted.

Figure 12:
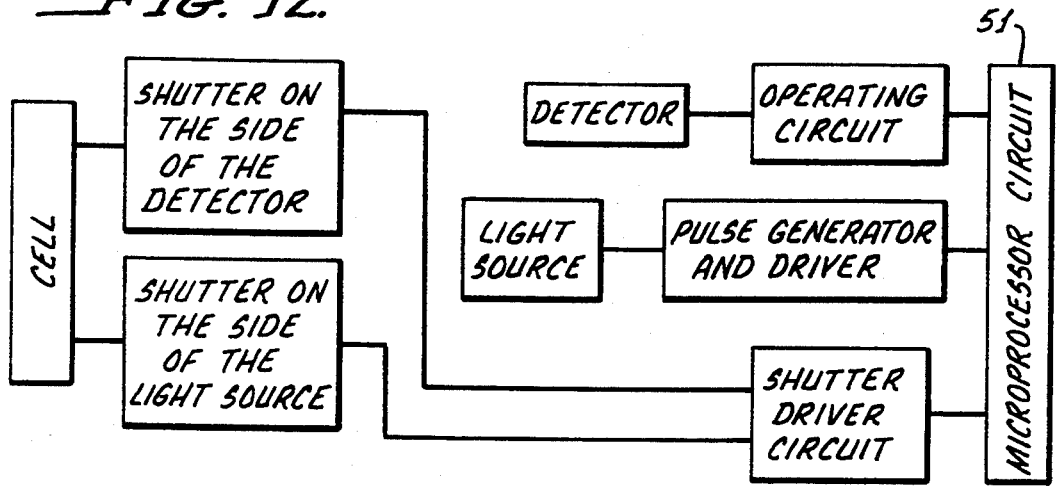
FIG. 12 is a block diagram showing one example of a control system in the infrared gas analyzer.

FIGS. 12 is a diagram showing one example of a circuit in the above-described infrared gas analyzer.

Next, operation of the infrared gas analyzer having the above-described construction is described with reference to FIG. 13.

Initially, before the start of the measurement, both the first shutter 24, on the side of the radiation source, and the second shutter 16, on the side of the detector, are in a closed configuration. That is to say, in first shutter 24, the opening 27A of the first shutter body 27 is positioned so as not to overlap an optical path of the infrared radiation emitted from the radiation source 8. The optical path of the infrared radiation is blocked, while, in the second shutter 16, on the side of the detector, the opening 27A of the shutter body 27 is positioned at a position different from the filters 15A, 15B of the detector 15, and thus the detector 15 is in a shaded condition.

1. When a button is operated to switch on the power source [refer to (c) in FIG. 13] in the above-described configuration, the radiation source 8 radiates, but the first shutter 24 on the side of the radiation source is closed, so that the infrared radiation does not pass through cell 1. At this time, the pump is driven to supply the inside of cell 1 with the sample gas. Although the surface temperature of the radiation source 8 is nearly 0° C. before the power source is switched on, the radiation source 8 is heated by switching on the power source to increase the temperature as shown by the curve 1 in FIG. 13.

2. The surface temperature of the radiation source is increased to a temperature suitable for the measurement of the component gas (for example, 350° C.). First shutter 24, on the side of the radiation source, is then opened [refer to (b) in FIG. 13] establishing optical communication between radiation source 8 and sample cell 1. At this time, second shutter 16, on the side of the detector, still remains closed interrupting optical communication between radiation source 8 and detector 15. Consequently, the infrared radiation transmitted through sample cell 1 is not registered by the detector 15.

3. The second shutter 16, is opened and closed twice at an interval of, for example, 10 seconds during the time when the first shutter 24, is open [refer to (b) in FIG. 13]. The second shutter 16 is opened for the time sufficient for measuring the component gas, for example, 1 second. By opening and closing the second shutter 16 optical communication is established and the infrared radiation emitted from the radiation source 8 and transmitted through the cell 1 intermittently registers upon the dual-type detector 15 provided with an element for use in the sample signal and an element for use in the reference signal. Two signals $S_1$, $S_2$ are generated by the detector 15, and the concentration of the component gas to be measured in the sample gas is obtained on the basis of the average value of the two signals $S_1$, $S_2$.

4. After completion of the measurement, the first shutter 24, on the side of the radiation source, is closed [refer to (b) in FIG. 13], and the power source for the radiation source 8 is simultaneously switched off [refer to (c) in FIG. 13]. In addition, at the same time, the second shutter 16, on the side of the detector, is closed [refer to (a) in FIG. 13]to prepare for the next measurement. The first shutter 24 is opened for the time necessary for the measurement of the component gas to be measured, for example, 10 seconds and over, and then closed [refer to (b) in FIG. 13]. The second shutter 16, is opened and closed several times during the period when the shutter 24 on the side of the radiation source is opened. Although the second shutter 16 is opened as soon as the first shutter 24 is opened, and subsequently closed after 1 second followed by being opened again after 9 seconds in the embodiment shown in FIG. 13, the present invention is not limited by this. That is to say, the above-described operation may be repeated a plurality of times.

Figure 13:
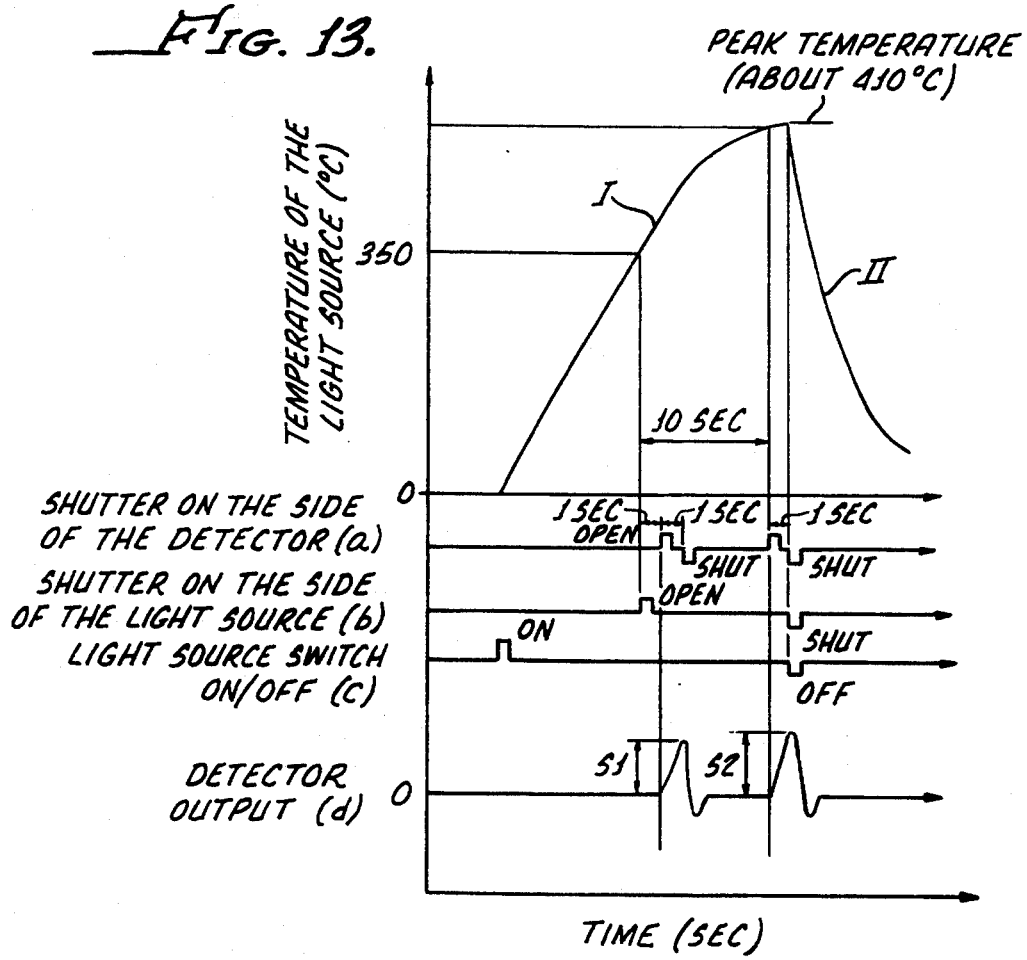
FIG. 13 is a graphical representation of the operation of an exemplary infrared gas analyzer of the present invention.

The surface temperature of the radiation source 8 continues to slightly increase after the supply of electric power to the radiation source 8 is stopped, and gradually decreases as shown by curve 11 in FIG. 13 after a peak (for example, 410° C.). Although it is desirable for the surface temperature of the radiation source 8 to be lowered to nearly room temperature following measurement, about 50° C. is sufficient.

The above-described steps 1 to 4 illustrate one measuring cycle which may be controlled by a microprocessor circuit 51 shown in FIG. 12. In short, the time until the surface temperature of the radiation source 8 arrives at the temperature suitable for the measurement, after the radiation source 8 is switched on, can be set in advance by the use of the radiating temperature-change characteristic graph as shown in FIGS. 6 and 7. Accordingly, the desired operation can be conducted by programming above-described steps 1 to 4 in the microprocessor circuit 51.

Although pulsed infrared radiation is emitted from the radiation source 8 in the above-described respective embodiments, the infrared radiation may be continuously emitted from the radiation source 8 to elevate the temperature to one suitable for the measurement, and the first shutter 24, on the side of the radiation source, and the second shutter 16, on the side of the detector, may be opened and closed under such conditions in the same manner as in the above-described preferred embodiments.

Figure 14:
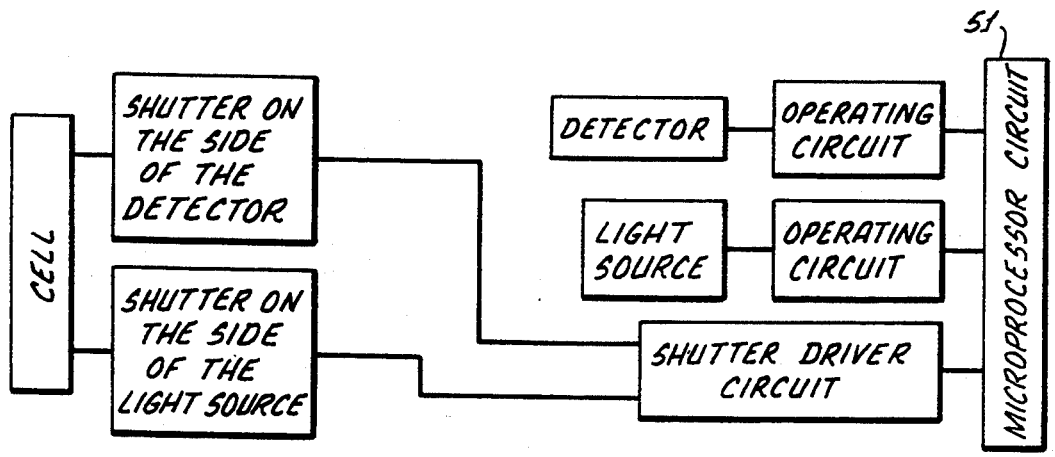
FIG. 14 is a block diagram showing another control system in an infrared gas analyzer.

FIG. 14 is a diagram showing one example of a construction of a circuit in such a case. In addition, FIG. 15 is a diagram showing movements of the respective portions and the change of the radiation source in temperature in the case where the measurement is conducted twice at a suitable interval.

Figure 15:
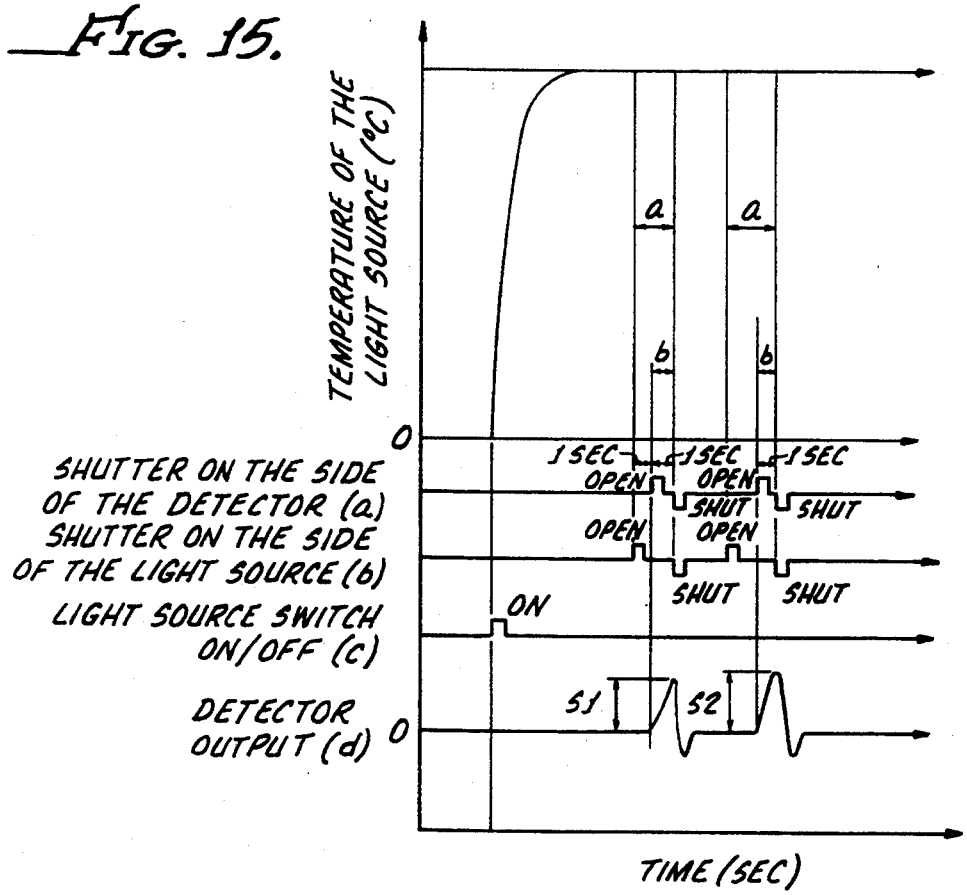
FIG. 15 is a graphical representation of the operation of an exemplary infrared gas analyzer of the present invention.

In the embodiment shown in FIG. 15, the operation of opening the second shutter 16, on the side of the detector, for 1 second during the time when the first shutter 24, on the side of the radiation source, is being opened is repeated twice at a suitable interval. Referring to FIG. 15, a designates the time which the radiation source is opened, and b designates a measuring time.

A sample cell may be bifurcated; that is, provided with two discrete cells. Thermal sensors, such as thermoresistor types and thermocouple types, various kinds of semiconductor sensors and pneumatic sensors, such as a condenser microphone type, may be used as the detector 12 in addition to the pyrosensors.

Moreover, a plurality of component gases to be measured can be simultaneously detected by providing a plurality of sensors and interference filters. In addition, although the interference filters are in general positioned immediately before the detector, they may be positioned between the radiation source 8 and the sample cell 1 or between the sample cell 1 and a shutter 11.

As described above, with the infrared gas analyzer according to the present invention, the concentration of $CO_2$ within a room can be measured not by continuously operating the radiation source or rotating the chopper but by applying power as necessary. The chopping can be conducted by opening and closing the shutter a plurality of times as occasion demands, so that intermittent or continuous measurements can be achieved. Furthermore, the time during which the radiation source is operative is reduced, as compared with the conventional infrared gas analyzers. In addition, the operating time of the shutter is remarkably short, so that the quantity of heat generated is reduced. Consequently, the influence of temperature upon the detector can be remarkably reduced, and thus the measurement can be achieved at higher accuracy with a substantial reduction in the consumption of energy.

The infrared gas analyzer according to the present invention is compact and easily handled, so as to provide simple operation, and can be easily used for the measurement of, for example, the concentration of $CO_2$ in homes, offices and the like.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. An infrared gas analyzer having low energy consumption, low temperature drift from self-heating, and small size; said infrared gas analyzer comprising:
   a sample cell containing a sample gas;
   a radiation source positioned adjacent to one end of said sample cell so that infrared radiation emitted by said radiation source may pass through said sample gas;
   an infrared detector positioned adjacent to an opposite end of said sample cell to receive infrared radiation after passage thereof through said sample gas;
   a shutter, having a linearly moving shutter body disposed between said radiation source and said detector and movable between an opened and a closed position, when opened said shutter establishing optical communication between said radiation source and said infrared detector; and
   means for moving said shutter from said closed position to said open position when said radiation source reaches a temperature suitable for measuring a component gas in said sample gas, and for subsequently closing said shutter after a predetermined measurement interval.

2. The infrared gas analyzer of claim 1 wherein said shutter is positioned between said radiation source and said sample cell.

3. The infrared gas analyzer of claim 1 wherein said shutter is positioned between said sample cell and said infrared detector.

4. The infrared gas analyzer of claim 1 wherein said radiation source is a resistor including a substrate of AlN and a resistance element selected from the group consisting of $RuO_2$, W, $SnO_2$, FeCrAlY, Pt, Pt-Rh, Pt-Pd, PTC materials containing $BaTiO_3$ and combinations thereof.

5. The infrared gas analyzer of claim 1 wherein said radiation source includes a heating resistor activated by electrical power and said electrical power and said shutter are interrelatedly controlled.

6. The infrared gas analyzer of claim 5 wherein said electrical power to said radiation source is terminated substantially simultaneously with the closing of said shutter body after said predetermined measurement interval.

7. The infrared gas analyzer of claim 6, wherein said infrared source incorporates a temperature sensor.

8. The infrared gas analyzer of claim 1 wherein said detector is selected from the group consisting of thermoresistor sensors, thermocouple sensors, semiconductor sensors, pneumatic sensors, and pyrosensors.

9. The infrared gas analyzer of claim 1 wherein said shutter body includes a shading portion provided between a pair of oppositely acting self-holding solenoids, said shading portion being moved by a connected pair of movable iron cores associated respectively with one of said pair of self-holding solenoids.

10. An infrared gas analyzer having low energy consumption, low temperature drift from self-heating, and small size; said infrared gas analyzer comprising:
    a sample cell containing a sample gas;
    a radiation source positioned adjacent to one end of said sample cell so that infrared radiation emitted by said radiation source may pass through said sample gas;
    an infrared detector positioned adjacent to another end of said sample cell opposite said radiation source;

a shutter, having a moving shutter body disposed between said radiation source and said sample cell and movable between an opened and a closed position, when opened said shutter establishing optical communication between said radiation source and said sample cell; and a second shutter, having a moving second shutter body disposed between said radiation source and said infrared detector and movable between an opened and a closed position, when opened said second shutter establishing optical communication between said sample cell and said infrared detector;

means for moving said shutter from said closed position to said open position when said radiation source reaches a temperature suitable for measuring a component gas in said sample gas; and means for moving said second shutter from said closed position to said open position and back again at least once prior to said shutter body being closed after a predetermined measurement interval, thereby establishing optical communication between said radiation source and said detector.

11. The infrared gas analyzer of claim 10 wherein said radiation source includes a resistor activated by electrical power and said electrical power and said shutter are interrelatedly controlled.

12. The infrared gas analyzer of claim 11 wherein said electrical power to said radiation source is terminated substantially simultaneously with the closing of said shutter body after said predetermined measurement interval.

13. The infrared gas analyzer of claim 12, wherein said infrared source incorporates a temperature sensor.

14. The infrared gas analyzer of claim 10 wherein said detector is selected from the group consisting of thermoresistor sensors, thermocouple sensors, semiconductor sensors, pneumatic sensors, and pyrosensors.

15. The infrared gas analyzer of claim 10 wherein said shutter body includes a shading portion provided between a pair of oppositely acting self-holding solenoids, said shading portion being moved by a connected pair of movable iron cores associated respectively with one of said pair of self-holding solenoids.

16. A cyclicly-operating infrared gas analyzer having low energy consumption, low temperature drift from self-heating, and small size; said infrared gas analyzer comprising:

an intermittently-operated electrically-heated infrared radiation source having one of a known characteristic of infrared-radiating-temperature-versus-time from the moment electrical power is applied thereto, or means for measurement of the infrared-radiating temperature of said infrared radiation source;

means for applying electrical power to said infrared radiation source in response to a turn-on signal, and for shutting off said electrical power to said infrared radiation source in response to a shut-off signal;

means for providing an output in response to one of: the passage of a selected time interval from said turn-on signal, or the attainment of a selected infrared-radiating temperature by said infrared radiation source;

a sample gas cell for receiving and containing a sample gas, and for transmitting infrared radiation from said radiation source therethrough;

a detector for receiving infrared radiation transmitted through said sample gas from said infrared radiation source and for responsively providing an indication of the concentration of a component gas therein;

a shutter movable to open and close optical communication of infrared radiation between said infrared radiation source and said detector via said sample cell and said sample gas therein; and shutter moving means for moving said shutter from a closed position to an open position in response to said output, and for both reclosing said shutter after a determined measurement time interval and simultaneously providing said turn-off signal;

whereby said gas analyzer operates in a cyclical manner each time an turn-on signal is provided by an operator of said analyzer to thereafter sequentially: heat said infrared radiation source, irradiate said sample gas with infrared radiation from said source, acquire said indication of the concentration of said component gas in said sample gas, and turn off electrical heating of said infrared radiation source.

17. The cyclicly-operating infrared gas analyzer of claim 16 wherein said shutter is disposed between said sample cell and said detector.

18. The cyclicly-operating infrared gas analyzer of claim 16 wherein said shutter is disposed between said sample cell and said infrared source.

19. The cyclically-operating infrared gas analyzer of claim 16 wherein said shutter body includes a shading portion provided between a pair of oppositely acting self-holding solenoids, said shading portion being moved by a connected pair of movable iron cores associated respectively with one of said pair of self-holding solenoids.

20. The cyclicly-operating infrared gas analyzer of claim 16 further including a second shutter movable to open and close optical communication of infrared radiation between said infrared radiation source and said detector via said sample cell and said sample gas therein.

21. The cyclicly-operating infrared gas analyzer of claim 20 wherein said second shutter is disposed between said sample cell and said infrared source, said shutter being disposed between said sample cell and said detector.

22. The cyclicly-operating infrared gas analyzer of claim 20 further including means for moving said second shutter from a closed position to an open position and back to a close position in coordination with said shutter, said shutter and said second shutter sandwiching said sample cell therebetween so that infrared radiation from said source reaches said detector through said sample gas only when both said shutter and said second shutter are open.

23. The cyclicly-operating infrared gas analyzer of claim 20 further including said shutter moving means including means for opening said second shutter before said shutter is opened, and for closing said shutter and said second shutter substantially simultaneously.

24. A sequentially-operating infrared gas analyzer which includes an electrically-heated infrared radiation source which is heated only intermittently in preparation for and during gas analysis, said infrared gas analyzer comprising:

an electrically-heated infrared radiation source having a known characteristic of infrared-radiating-temperature-versus-time from the moment electrical power is applied thereto;

means for applying electrical power to said infrared radiation source in response to a turn-on signal, and for disconnecting said electrical heating power from said infrared radiation source in response to a turn-off signal;

time interval means for providing an output in response to the passage of a selected warm-up time interval from said turn-on signal;

a sample gas cell for receiving and containing a sample gas, and for transmitting infrared radiation from said radiation source therethrough;

a detector for receiving infrared radiation transmitted through said sample gas from said infrared radiation source and for responsively providing an indication of the concentration of a component gas therein;

a first shutter and a second shutter each disposed at a respective one of said infrared radiation source and said detector, and each movable to close optical communication of infrared radiation between said infrared radiation source and said detector via said sample cell and said sample gas therein; said shutters allowing said optical communication of said infrared radiation from said infrared radiation source to said detector via said sample gas only when both are moved to an open position; and controller means including shutter moving means responsive to said output for thereafter moving said first and second shutters individually from a closed position to an open position, and for reclosing said shutters after respective time intervals to obtain a first and subsequent indications of the concentration of said component gas in said sample gas, and for thereafter providing said shut-off signal;

whereby said gas analyzer operates to sequentially: heat said infrared radiation source during the warm-up time interval following the providing of said turn-on signal by an operator, and thereafter irradiates said sample gas a first time with infrared radiation from said source by sequential operation of said first and second shutters to provide a first time interval during which both are open, acquires a respective first indication of the concentration of said component gas in said sample gas, and irradiates said sample gas a second or subsequent times by another or subsequent sequential operation of said first and second shutters to provide a second or subsequent time intervals during which both shutters are open, and acquires respective second or subsequent indications of the concentration of said component gas in said sample gas, followed by providing of said shut-off signal.

25. A low energy consumption, low temperature drift, method for determining the concentration of a component gas present in a sample gas comprising:

in response to a turn-on signal applying electrical heating power to an electrically-heated infrared radiation source;

heating said infrared radiation source to a selected infrared-radiating temperature thereby generating infrared radiation;

opening a shutter in response to attainment of a selected infrared-radiating temperature by said radiation source;

transmitting infrared radiation from said radiation source to an infrared detector through a sample cell and sample gas therein by opening of said shutter;

receiving infrared radiation transmitted through said sample gas from said infrared radiation source and responsively providing an indication of the concentration of a component gas therein; and closing said shutter after a determined measurement interval thereby interrupting said optical communication between said radiation source and said detector.

26. The low energy consumption, low temperature drift, method of claim 25 further comprising the step of shutting off said electrical heating power to said infrared radiation source substantially simultaneously with closing of said shutter whereby the method is cyclical.

27. The low energy consumption, low temperature drift, method of claim 25 further including the step of disposing said shutter between said sample cell and said detector.

28. The low energy consumption, low self-heating temperature drift, method of claim 25 further including the step of disposing said shutter between said sample cell and said infrared source.

29. The low energy consumption, low temperature drift, method of claim 25 further including the step of providing a second shutter movable to open and close optical communication of infrared radiation between said radiation source and said infrared detector via said sample cell and said sample gas therein.

30. The low energy consumption, low temperature drift, method of claim 29 further including the step of disposing said second shutter between said sample cell and said infrared source, said shutter being disposed between said sample cell and said detector.

* * * * *